United States Patent [19]

Sakuragi et al.

[11] Patent Number: 4,554,835
[45] Date of Patent: Nov. 26, 1985

[54] AUTOMATIC FLAW DETECTION DEVICE

[75] Inventors: Toshio Sakuragi, Kobe; Kazuo Nakayama, Hyogo; Masaaki Sato, Kamakura; Mitsuhiro Koike, Yokohama, all of Japan

[73] Assignee: Mitsubishi Denki Kabushiki Kaisha, Tokyo, Japan

[21] Appl. No.: 590,449

[22] Filed: Mar. 16, 1984

[30] Foreign Application Priority Data

Mar. 19, 1982 [JP] Japan ............... 57-45091

[51] Int. Cl.⁴ .............................. G01N 29/04
[52] U.S. Cl. ........................... 73/640; 73/641
[58] Field of Search ............... 73/641, 637, 638, 640, 73/622

[56] References Cited

U.S. PATENT DOCUMENTS

| | | | |
|---|---|---|---|
| 3,415,111 | 12/1968 | Chattaway et al. | 73/641 |
| 3,533,281 | 10/1970 | Hetherington | 73/641 |
| 3,791,201 | 2/1974 | Dory | 73/640 |
| 3,854,326 | 12/1974 | Hetherington et al. | 73/641 |

Primary Examiner—Stephen A. Kreitman
Attorney, Agent, or Firm—Oblon, Fisher, Spivak, McClelland & Maier

[57] ABSTRACT

An automatic flaw detection apparatus comprises a supporting frame; a hollow shaft which is supported on said frame in a freely rotatable manner through a bearing, and through the interior of which passes a material to be inspected; a holder disposed within said hollow shaft, and extending in the longitudinal direction of the axis of said hollow shaft, and rotating in association with said hollow shaft; sensing means incorporated in said holder to detect any defect in said material to be probed; and a signal transmission device interposed between said hollow shaft and said supporting frame, and to transmit the flaw detection signal from said sensor means to outside.

3 Claims, 3 Drawing Figures

AUTOMATIC FLAW DETECTION DEVICE

BACKGROUND OF THE INVENTION

1. Field of the Invention

This invention relates to an ultra-sonic automatic flaw detection device which detects automatically any defects in a material to be probed such as steel material, etc. by use of, for example, an ultra-sonic searching unit as a sensor.

2. Description of Prior Art

As a device of this kind, there has so far been known such one as shown in FIG. 1 of the accompanying drawing.

In the drawing, a reference numeral 1 designates a supporting frame which supports the entire device; a numeral 2 refers to a bearing supporter mounted on the supporting frame 1; a numeral 3 refers to a hollow shaft which is fitted and supported in a freely rotatable manner on this bearing supporter 2 through bearings 4, 4 such as, for example, ball bearings, etc., and through the interior of which passes a material 5 to be probed. The bearings 4, 4 are disposed in the neighborhood of both end parts of the hollow shaft 3. A numeral 6 refers to a signal transmission device which is interposed between the bearing supporters 2, 2, confronts to the hollow shaft 3, and transmits flaw detection signals from ultra-sonic searching units 9 to be mentioned later to the outside. The signal transmission device 6 is constructed with a rotor section 6a mounted on and around the outer periphery of the hollow shaft 3 between the bearings 4, 4 and a stator section 6b fixed on the supporting frame 1 in a manner to be opposite to the rotor section 6a, both these sections being made electrically cooperative. A reference numeral 7 designates a flaw detection signal repeater mounted on one end part of the hollow shaft 3. A reference numeral 8 designates a holder for searching units, which extends in the axial direction and opposite to the hollow shaft 3 through the flaw detection signal repeater 7, and rotates in association with rotation of the hollow shaft 3. A numeral 9 refers to a sensor comprising ultra-sonic searching units incorporated in the searching unit holder 8 (the sensor will hereinafter be called "ultra-sonic searching unit"). A reference numeral 10 denotes a water supply device which is mounted on the bearing supporter 2 at the other end part of the hollow shaft 3, and is to supply water for the flaw detection into a space gap between the ultra-sonic searching units 9 and the material 5 to be probed through a water supply passage formed consecutively in the hollow shaft 3, the flaw detection signal repeater 7, and the searching unit holder 8. A reference numeral 11 represents a belt pulley which is fitted on and around the outer periphery of the hollow shaft 3 at the other end part thereof; a numeral 12 refers to a drive motor mounted on one part of the supporting frame 1; a reference numeral 13 designates a belt extended between the rotational shaft of the drive motor 12 and the belt pulley 11; and a numeral 14 refers to pinch rollers to perform alignment of the material 5 to be probed.

In the following, the operations of the conventional automatic flaw detection device of the above-described construction will be explained. The ultra-sonic automatic flaw detection device is installed in a inspection line for the material 5 to be probed, such as steel material, so that the materials may pass sequentially through it. First of all, the drive motor 12 is actuated to rotate the hollow shaft 3 through the belt 13 and the belt pulley 11. In association with rotation of this hollow shaft 3, there rotate both searching unit holder 8 mounted on the hollow shaft 3 through the flaw detection signal repeater 7 and the ultra-sonic searching units 9 embedded in the searching unit holder 8. In the next place, a material 5 to be probed is conveyed from the inspection line and passes through the center of the searching unit holder 8 after alignment of the material 5 to be probed by way of the pinch rollers 14, 14. During passage of the material 5 to be probed through the center of the searching unit holder 8, water for the flaw detection is supplied from the water supply device 10 so as to fill the space gap between the ultra-sonic searching units 9 and the material 5 to be probed. By thus causing the material 5 to be probed to pass through the center of the searching unit holder 8 in rotation, the material 5 to be probed is sensed in a spiral form by means of the ultra-sonic searching units 9 embedded in the searching unit holder 8. The flaw detection signals from the ultra-sonic searching units 9 are transmitted from the rotor section 6a of the signal transmission device 6 to the stator section 6b through the flaw detection signal repeater 7, and then led outside.

With the above-described conventional device, however, the searching unit holder 8 extends in the longitudinal direction of and opposite to the hollow shaft 3, that is, it is mounted outwardly of the device in a jut-out condition, with the consequent elongation of the total length of the device. Accordingly, the spacing for arranging the pinch rollers 14, 14 becomes wide, and, when the distal end of the material 5 to be probed is about to pass through the searching unit holder 8 as shown in FIG. 3, if flexure or curving of the material 5 to be probed is large, it gets in contact with the searching unit holder 8 to make it impossible to carry out the flaw detection, and various other disadvantages.

SUMMARY OF THE INVENTION

The present invention has been made in view of the disadvantages inherent in the conventional device as mentioned in the foregoing, and aims at providing an automatic flaw detection device capable of shortening the total length of the device by disposing inside the hollow shaft the searching unit holder having the sensors embedded therein and rotating in association with the hollow shaft and by extending the same in and along the axial direction thereof.

According to the present invention in general aspect of it, there is provided an automatic flaw detection device, characterized by comprising: a supporting frame; a hollow shaft which is supported on said frame in a freely rotatable manner through a bearing, and through the interior of which passes a material to be probed; a holder disposed within said hollow shaft, and extending in the longitudinal direction of the axis of said hollow shaft, and rotating in association with said hollow shaft; sensing means incorporated in said holder to detect any defect in said material to be probed; and a signal transmission device interposed between said hollow shaft and said supporting frame to transmit the flaw detection signal from said sensor means to outside.

The foregoing object, other objects as well as the specific construction and function of the automatic flaw detection device according to the present invention will become more apparent and understandable from the following detailed description of a preferred embodiment thereof, when read in conjunction with the accompanying drawing.

BRIEF DESCRIPTION OF THE ACCOMPANYING DRAWING

DETAILED DESCRIPTION OF A PREFERRED EMBODIMENT

Figure 1:
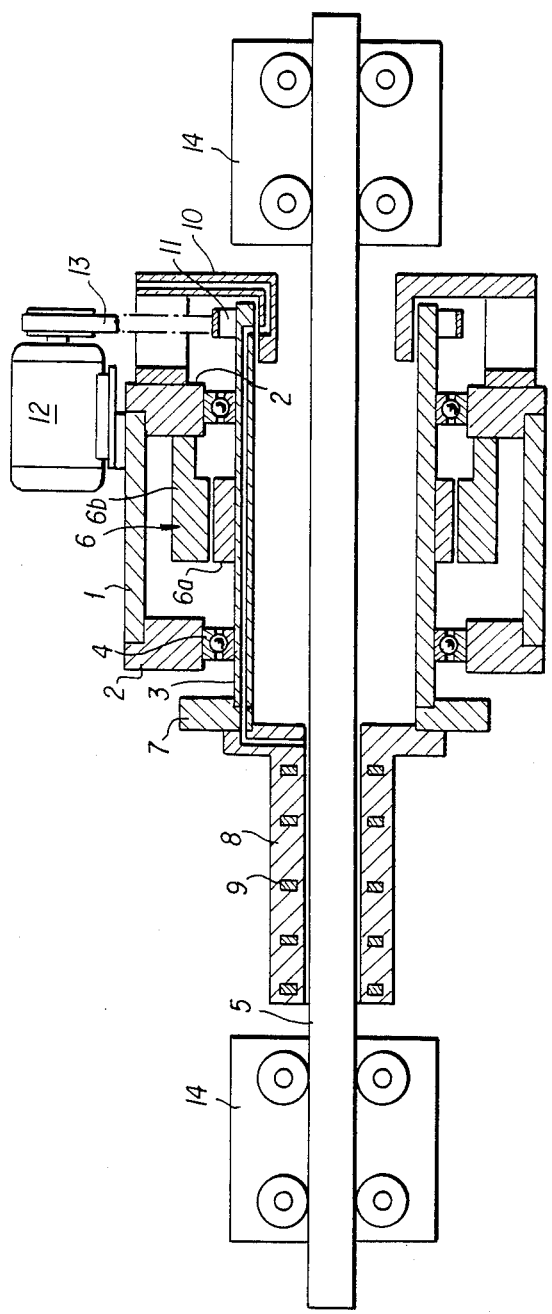
FIG. 1 is a longitudinal cross-sectional view showing a conventional automatic flaw detection device.
Figure 2:
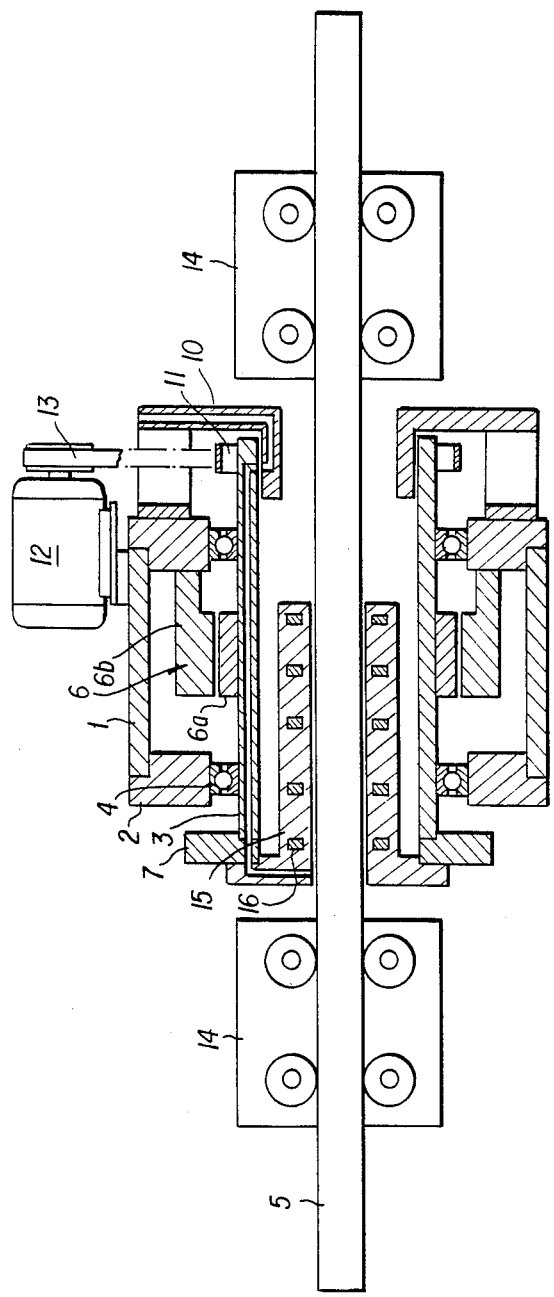
FIG. 2 is also a longitudinal cross-sectional view showing one embodiment of the automatic flaw detection device according to the present invention.

In the following, the present invention will be described in specific details with reference to a preferred embodiment thereof as shown in FIG. 2.

In the drawing, reference numerals 1 through 7 and 10 through 14 designate the exactly same component elements as in the above-described conventional automatic flaw detection device. A reference numeral 15 designates a holder for probing or searching units, which is disposed inside the hollow shaft 3 through the flaw detection signal repeater 7, extending along the longitudinal direction of the hollow shaft 3, and which rotates in association with the hollow shaft 3. A numeral 16 refers to sensors, each being constructed with an ultra-sonic searching unit and incorporated in the holder 15 (the sensor will hereinafter be referred to as "ultra-sonic searching unit").

In the following, the operations of the automatic flaw detection apparatus according to the present invention will be described. First of all, the drive motor 12 is actuated to rotate the hollow shaft 3 through the belt 13 and the belt pulley 11. In association with rotation of this hollow shaft 3, there rotate both searching unit holder 15 which is disposed inside the hollow shaft 3 extending in the longitudinal direction thereof through the flaw detection signal repeater 7 and ultra-sonic searching units 16 incorporated in the searching unit holder 15. Subsequently, the material 5 to be probed is conveyed from the inspection line and passed through the center of the searching unit holder 15 upon alignment of the material 5 to be probed by means of the pinch rollers 4. When the material 5 to be probed is passing through the center of the searching unit holder 15, water for the flaw detection is supplied from the water supply device 10 into a space gap between the ultra-sonic searching units 16 and the material 5 to be probed, and filled in it. Thus, by passage of the material 5 to be probed through the center of the searching unit holder 15 in rotation, the material 5 to be probed is searched in a spiral form by the ultra-sonic searching units 16 incorporated in the searching unit holder 15. The flaw detection signals from the ultra-sonic searching units 16 are transmitted from the rotor section 6a of the signal transmission device 6 to its stator section 6b by way of the flaw detection signal repeater 7, after which it is led outside.

Figure 3:
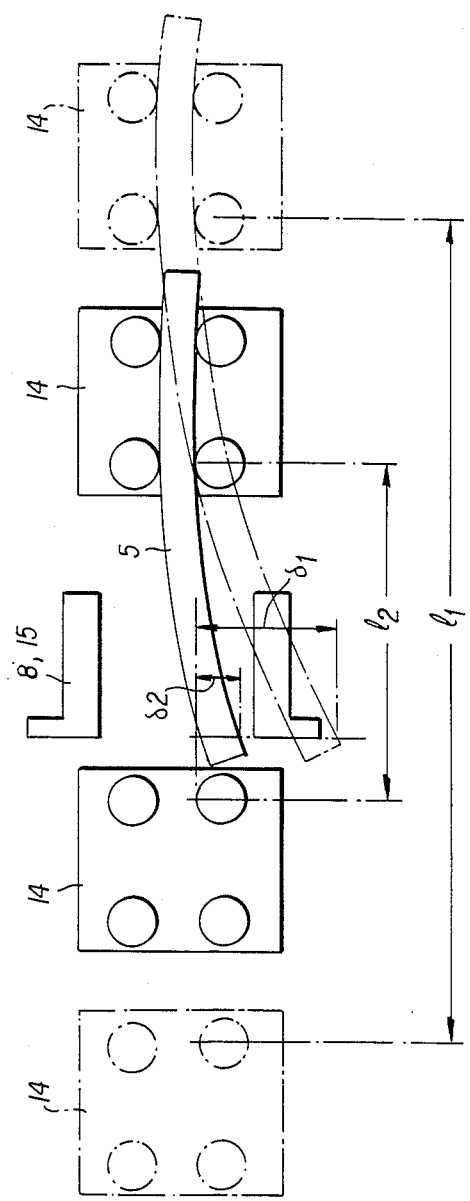
FIG. 3 is a schematic side view showing modes of curving of the material to be probed.

Incidentally, since the searching unit holder 15, in which the ultra-sonic searching units 16 are incorporated, is disposed inside the hollow shaft 3 extending along the lengthwise direction thereof, the total length of the device can be made short. Along with this shortening of the length of the flaw detection device, the spacing for arranging the pinch rollers 14, 14 is also shortened from $l_1$ to $l_2$ as shown in FIG. 3, whereby the deflecting quantity of the material 5 to be probed due to its curving can also be made small from its value $\delta_1$ to $\delta_2$, hence the material 5 to be probed can be searched without its getting in contact with the searching unit holder 15. Further, it is feasible with this device to perform search of the material 5 to be probed with its permissible amount of deflection or curving having been made large.

Incidentally, the signal transmission device 6 in the above-described embodiment may be constructd in such a manner that the rotor section 6a is made of a slip-ring and the stator section 6b of a brush. Or, it may be constructed in such a manner that the rotor section 6a is made of a rotary winding and the stator section 6b of a fixed winding. In either case, there can be obtained the same effect as that of the above-described embodiment.

In the above-described embodiment according to the present invention, explanations have been made as to the automatic flaw detection device by use of the ultrasonic probing technique. It should, however, be noted that the present invention is not limited to this embodiment alone, but it is applicable to other probing techniques. For example, the present invention is also applicable to an automatic flaw detection device by use of the magnetic probing technique, an automatic flaw detection device by use of the electrical probing technique, an automatic flaw detection device by use of the optical probing technique, and so forth.

As has been described so far, according to the present invention, the automatic flaw detection device of a shortened total length can be realized by disposing the searching unit holder inside the hollow shaft and extending along the longitudinal direction thereof.

Although the present invention has been described in the foregoing with particular reference to the preferred embodiment thereof, it should be noted that any changes and modifications may be made by those persons skilled in the art without departing from the spirit and scope of the invention as recited in the appended claims.

What is claimed is:

1. An ultrasonic automatic flaw detection apparatus comprising:
    (a) a supporting frame;
    (b) a hollow shaft journaled in said supporting frame by axially spaced bearings located near the axial ends of said hollow shaft;
    (c) a signal transmission device disposed within said supporting frame between said axially spaced bearings, said signal transmission device comprising a rotor section mounted on and circumferentially surrounding said hollow shaft and a stator section mounted on said supporting frame and operatively connected to said rotor section;
    (d) a flaw detection signal repeater mounted on said hollow shaft axially downstream of the downstream one of said bearings with reference to the direction the material to be inspected passes through said hollow shaft during use of the apparatus;
    (e) a holder for ultrasonic searching units coaxially disposed within said hollow shaft and rotatable therewith, said holder extending through said flaw detection signal repeater and extending axially upstream from said flaw detection signal repeater in said hollow shaft to a point upstream of said signal transmission device, said holder having an axial through bore through which, during use of the apparatus, the material being inspected passes with a clearance between the outer periphery of the material being inspected and the inner periphery of said holder;
(f) a plurality of ultrasonic searching units mounted in said holder for ultrasonic searching units at axially spaced intervals within said hollow shaft;
(g) a water supply means mounted on said supporting frame for supplying water to the clearance between the said holder for ultrasonic searching units and the material being inspected; and
(h) drive means for rotating said hollow shaft, said rotor section, and said flaw detection signal repeater.

2. An ultrasonic automatic flaw detection apparatus as recited in claim 1 wherein said signal transmission device comprises a brush and a slip-ring.

3. An ultrasonic automatic flaw detection apparatus as recited in claim 1 wherein said signal transmission device comprises a rotary winding mounted on said hollow shaft and a fixed winding mounted on said supporting frame.

* * * * *